United States Patent [19]

Ghosh et al.

[11] 4,022,665
[45] May 10, 1977

[54] TWO PHASE ANAEROBIC DIGESTION

[75] Inventors: Sambhunath Ghosh, Chicago; Donald L. Klass, Barrington, both of Ill.

[73] Assignee: Institute of Gas Technology, Chicago, Ill.

[22] Filed: Dec. 9, 1974

[21] Appl. No.: 530,760

[52] U.S. Cl. .................................. 195/27; 195/104; 195/144
[51] Int. Cl.[2] .......................................... C12D 3/10
[58] Field of Search ............. 195/27, 104, 28 R, 2, 195/3 R

[56] References Cited

UNITED STATES PATENTS

| 1,990,523 | 2/1935 | Buswell et al. | 195/27 |
| 3,640,846 | 2/1972 | Johnson | 195/27 |

OTHER PUBLICATIONS

Pohland, et al.; Biotechnol. and Bioeng. Symp. No. 2, by John Wiley & Son Inc. (1971).

*Primary Examiner*—Alvin E. Tanenholtz
*Attorney, Agent, or Firm*—Dominik, Knechtel, Godula & Demeur

[57] ABSTRACT

An improved two phase anaerobic digestion process in which an initial phase continually receives an organic feed for short detention times of less than two days under conditions which efficiently liquefy and breakdown the feed to lower molecular weight acids and other intermediates for conversion to methane. A succeeding phase is operated to treat the lower molecular weight acids and intermediates for detention times of about two to about seven days under conditions which efficiently lead to production of methane. The feed is loaded in the first phase at rates from about 1 to about 10 pounds of total organics per cubic foot per day; and the products from the initial phase are loaded in the succeeding phase at rates of about 0.1 to about 0.5 pounds total organics per cubic foot per day.

10 Claims, 1 Drawing Figure

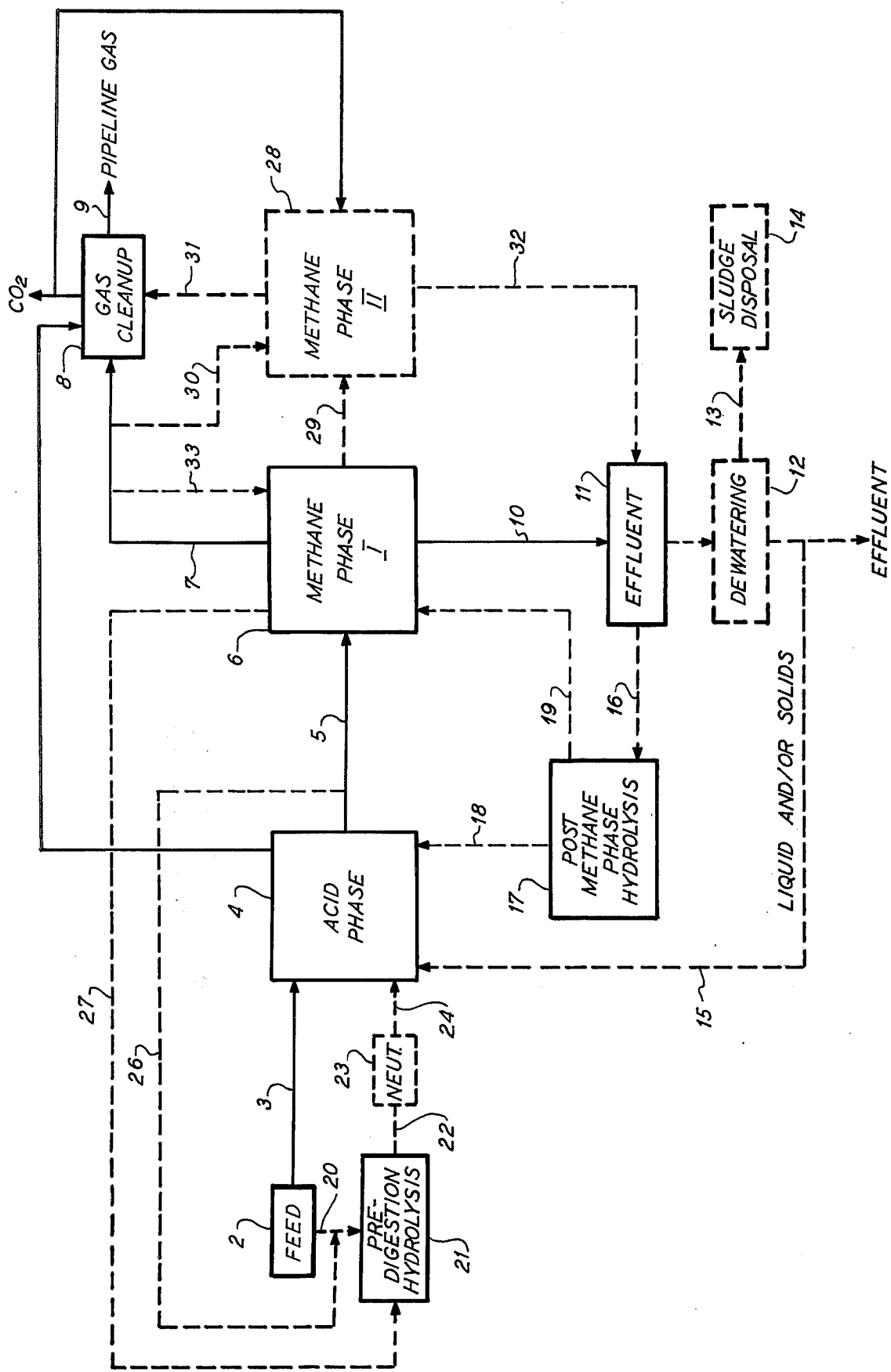

TWO PHASE ANAEROBIC DIGESTION

This invention relates to an improved treatment of organic waste to more efficiently collect methane for pipeline or fuel gas. The invention particularly relates to an improved two phase procedure wherein conditions are provided to efficiently conduct an acid forming phase and to separately conduct a methane production phase.

Feed sludge mixtures are commonly subjected to anaerobic digestion wherein the organic waste is digested by micro-organisms in the absence of oxygen. Such feed sludge mixture may be raw sewage sludge or municipal refuse treated alone or in combination with raw sewage sludge. Municipal refuse primarily contains cellulosic products, particularly kraft paper. It is known that such cellulosics can be digested as well as the minor amounts of waste protein, carbohydrates and fat present in such municipal refuse. Such refuse is conventionally shredded and subjected to various separation steps to remove ferrous scrap and non-ferrous metals, such as glass. A useful procedure is to combine such shredded and separated refuse with raw sewage sludge by blending and then separating grit. The blended sludge feed mixture is then delivered as a slurry to a digester.

Anaerobic digestion is often used in combination with primary and activated sludge and/or trickling filter treatment to treat municipal liquid wastes, that is, raw sewage. The activated sludge or trickling filter treatment is, of course, conducted in the presence of oxygen. Raw sewage may be moved through a primary settling tank to obtain a primary sludge feed containing up to about 2% solids; and the settled sewage may then be moved to an activated sludge area to collect a secondary sludge feed containing less than about 1% solids. Such combined primary and secondary sludge feeds can then be delivered to an anaerobic digester. It may be estimated that about 80% of such solids are organics, the majority of which are biodegradable. The organics are subjected to successive acid and methane fermentation steps. The evolved methane and carbon dioxide gases are collected, and the liquid together with the digested or stabilized sludge is dewatered and disposed. An attractive approach to anaerobic digestion involves separated two phase acid and methane digesters, such as described by Pohland and Ghosh, Biotechnol and Bio-Eng. Symp. No. 2, 85–106 (1971), John Wiley & Sons, Inc.; and by the same authors in Environmental Letters, 1 (4), 255–266 (1971), Marcel Dekker, Inc.

It is an object of this invention to improve methane or pipeline gas production under treatment conditions which assure high biochemical oxygen demand (BOD) removal.

Another object of the present invention is to collect increased amounts of methane gas from anaerobic digestion of organic wastes under improved conditions of stabilizing waste products so that problems of disposing of liquid and solid effluents are reduced.

Still another object of the present invention is to obtain higher efficiencies in anaerobic digestion of organic wastes by separating an acid-forming phase from a methane-forming phase so that each phase can be operated more efficiently to attain greater advantages in the overall anaerobic digestive process for producing methane gas and stabilizing organic wastes.

Yet another object of the present invention is an improved method and system for producing methane gas by anaerobic digestion of organic wastes wherein a separate acid-forming phase leads to improved liquefaction and denitrification of liquid wastes; and a separate methane-forming phase results in improved methanation of the organic wastes, as well as methanation of carbon dioxide which is formed as a by-product.

Still yet another object of the present invention is the utilization of separate acid-forming and methane-forming phases in anaerobic digestion with provisions of particular detention times and loading rates in each phase to improve the overall process. In a further aspect, provisions are made for recycling formed carbon dioxide and collected wastes to further increase the efficiency of the process with respect to methane production and waste stabilization.

The foregoing objects are now accomplished together with still other objects which will occur to practitioners by the invention of the present disclosure. The invention utilizes a separate acid digestion phase wherein fermentation under anaerobic conditions leads to the production of aldehydes, alcohols and acids. A small amount of carbon dioxide is formed in such a separate acid forming phase and is routed to a separate methane phase where the carbon dioxide is methanated. A small amount of produced methane from the acid phase may also be delivered to the methane phase for later conveyance to collection means. The fermentation in the methane phase leads to the production of methane and carbon dioxide, and these gases may be directed to a clean-up zone from which the methane is moved into the collection means and the carbon dioxide is recycled to the methane phase. Such recycling provides additional material for methanation in the methane stage, and also physically agitates the mixture in the methane stage through a bubbling action. Organic feed leaves the methane phase through a separator zone where liquid effluent may be either discharged or recycled to the acid stage. Sludge from the separator zone may be recycled to the methane stage for further methanation treatment, or it may be chemically or thermally treated to make it more biodegradable before recycling.

Such objects are in particular accomplished by maintaining the phases in overall shortened detention times of less than about ten days. In the preferred form, the detention time in the acid phase is from about ½ day to about 1½ days. The organic feed is delivered from the acid phase to a methane phase, and such feed contains lower molecular weight acid compounds and other intermediate products, such as aldehydes and alcohols. This feed is detained in a methane phase for about two days to about seven days. The feed to the methane phase may be intermittent or continuous, whereas the feed to the acid phase is continuous. The separate phase digestion allows increased loading rates in that loading in the acid phase is from about one to about 10 pounds of total organics per cubic foot per day; whereas loading in the methane phase is from about 1/10 to about ½ pounds of total organics per cubic foot per day.

The method also contemplates the selective use of predigestion hydrolysis of the organic waste before introduction into the acid phase, as well as post-methane hydrolysis of waste removed from the methane phase. The hydrolysis can be conducted as mild acid or mild alkaline hydrolysis, followed by neutralization of the added acid or alkali. The acid phase pH is maintained from about five to about 6; and the methane phase pH is maintained from about 6.8 to about 7.4.

In another aspect of the invention, the methane phase can comprise a plurality of methane digester phases. This is performed to more efficiently utilize particular microorganisms with particular compounds or substrates. For example, a second methane digester can be provided to enrich a methane former such as *Mb. omlianskii* which efficiently reduces recycled carbon dioxide to methane. It has been found that such carbon dioxide reducing methane formers are not enriched in a first methane digester which appears preferentially to enrich a volatile-acid-utilizing methane bacteria such as *Mb. suboxydans*, *Methanosarcina bovekeri*, *Mb. propionicum*, and *Methanosarcina methanica*, and the like. When a plurality of methane digesters are used there is created the possibility of sulfide toxicity, as where sulfides are formed from the sulfuric acids which can be used in mild acid hydrolysis, or which may be present in the feed itself. Such sulfides are reacted with neutralizing salts such as ferric chloride. It has been found that such sulfide neutralizing salts tend to reduce any hydrogen sulfide present in the digester gases. Such neutralization reduces the cost of gas clean-up.

It has become generally recognized that certain requirements promote waste stabilization in conventional digesters, these requirements may be summarized as:

| | |
|---|---|
| pH | 6.5–7.5 |
| Temperature | 85°–100° F |
| Dissolved Oxygen | small as possible |
| Alkalinity | 1000–5000 mg/ bicarbonate as (CaCO$_3$) |
| Nutrients | N, P, K, and trace elements |
| Loading | about 0.1–0.4 lb. volatile solids/CF digester cap. - day |
| Retention Time | 15–40 days |

Practitioners may advert to such recognized requirements to practice the present invention recognizing, of course, that the retention time will be divided between the separate acid and methane forming stages.

It is also recognized that one of the major component of urban solid waste is kraft paper which can be digested at levels over 90% under recognized anaerobic digestion. The cellulosic destruction efficiency by anaerobic digestion is generally high, except for wood which is not digestible unless treated to make it more biodegradable. Reference may be made to the publication "Anaerobic Digestion of Solid Waste," *News Quarterly*, Vol. 20, April, 1970, University of California, Berkeley. The improved features of the present invention may, therefore, be realized in processing municipal refuse as the sludge feed mixture, alone or in combination with raw sewage sludge. Such raw sewage may, of course, be processed through a preliminary activated sludge treatment.

The microorganisms which ferment the organic wastes under anaerobic conditions require few conditions for adequate activity. Such requirements have been referred to previously, and generally require the usual nutritive salts, carbon dioxide, a reducing agent, a single oxidizable compound suitable for the organism, and a source of nitrogen. See for example, Mylroie and Hungate, *Can. J. Microbiology*, Vol. 1. pp. 55-64 (1954). Several species of methane producing bacteria have been reported, including:

*Methanobacterium omelianskii*
*Mb. formicicum*
*Methanosarcina barkerii*
*Mb. sohngenii*
*Ms. methanica*
*Mc. mazei*

A wide variety of substrates are utilized by the methane-producing bacteria, but each species is believed to be characteristically limited to the use of a few compounds. It is therefore believed to be characteristically limited to the use of a few compounds. It is therefore believed that several species of methane-producing bacteria are required for complete fermentation of the compound present in sewage. In fact, mixed cultures are required for complete fermentation. For example, the complete fermentation of valeric acid requires as many as three species of methane-producing bacteria. Valeric acid is oxidized by *Mb. suboxydans* to acetic and propionic acids, which are not attacked further by this organism. A second species, such as *Mb. propionicum*, can convert propionic acid to acetic acid, carbon dioxide, and methane. A third species, such as *Methanosarcina methanica*, is required to ferment acetic acid.

An operative mixed culture is capable of maintaining itself indefinitely as long as a fresh supply of organic materials is added because the major product of the fermentation are gases, which escape from the medium leaving little, if any, toxic growth inhibiting products.

Various studies in the art have demonstrated that a number of acids are converted to methane and carbon dioxide when such acids are contacted with mixed anaerobic cultures. For example, the fermentation of acetic, propionic, and butyric acids, as well as ethanol and acetone, all result in the production of methane and carbon dioxide. Only the ratio of methane to carbon dioxide can change with the oxidation state of the particular substrate. Studies in the art have also established that carbon dioxide can be methanated by the oxidation of hydrogen. It has even been suggested that methane fermentation of an acid, such as acetic, is a two step oxidation to form carbon dioxide and hydrogen followed by a reduction to form methane. The net result is the production of methane and carbon dioxide. The art has also supposed that carbon dioxide could be converted to methane in a step by step reduction involving formic acid or carbon monoxide, formaldahyde and methanol as intermediates. Whatever the actual underlying mechanism, it is accepted that carbon dioxide can participate in the methanation process.

Reference may now be made to the drawing which is a highly schematic block diagram illustrating representative embodiments of the invention, the dotted lines representing alternative embodiments. A source of organic waste feed 2 is delivered along line 3 to an acid phase digester 4. The organic feed may be waste such as manure, municipal refuse, raw sewage, primary sludge, activated sludge, or any combination. The organic feed may also be a biomass of land or water base plants, such as trees, grass, kelp, algae and the like. The term "organic feed" shall refer to both organic waste and organic biomass. The mode of operation provides continuous feed along line 3 into the acid phase, and continuous or intermittent agitation of the organic waste in the acid phase digester. The organic waste is kept in the acid phase for a detention time of about ½ to 1½ days at a pH of about 5 to about 6. The organic waste is continuously loaded into the acid phase at a rate of 1 to about 10 pounds of total organics per cubic foot per day.

The liquid effluent from the first phase is then delivered along line 5 to a separate methane phase digester 6, and such delivery may be intermittent or continuous at a loading rate of about 0.1 to about 0.5 lbs. of total organics per cubic foot per day. The acid waste is gently agitated in the methane phase and the detention time of such waste in the methane phase is from about 2 to about 7 days over a pH range of about 6.8 to about 7.4. The formed gases consisting principally of carbon dioxide and methane are moved along line 7 to a gas clean-up zone 8, and thereafter conveyed to pipeline 9 for delivery to a fuel utilization means.

The effluent is moved through line 10 to a collection zone 11. Such effluent may be processed by dewatering at 12 and conveying the sludge cake along line 13 to a sludge disposal station 14. In the alternative, the effluent may be conveyed along line 15, with or without dewatering, for recycling to the acid phase 4. Such effluent can comprise liquid alone, solids alone, or a mixture of liquids and solids.

In another alternative embodiment, the effluent from station 11 can be conveyed along line 16 to a post hydrolysis zone 17 where mild hydrolysis can occur by acid or alkaline treatment. The post hydrolysed effluent can then be recycled along line 18 to the acid phase 4. In the alternative, the hydrolysed effluent from the methane digester can be delivered along line 19 back to the methane phase digester 6. A neutralization station (not shown) may be interposed in lines 18, 19 prior to return to their respective phase digesters.

In the preferred practice, the feed from source 2 is moved in a stream along line 20 to a predigestion hydrolysis zone 21 where mild acid or alkaline hydrolysis occurs. The hydrolysed feed is then moved along line 22 to a neutralization zone 23 where either the acid or alkaline is neutralized; and the stream is then moved along line 24 to the acid phase digester 4. The stream of acid waste may be taken from line 5 and moved along line 26 for recycling to the prehydrolysis zone 21 along line 20. Similarly, effluent from the methane phase digester 6 can be returned along line 27 to the predigestion zone 21. Recycling the acid phase and methane phase effluents results in successive neutralization, enhanced hydrolysis, and dilution, as well as improved acidification in the acid phase and gasificatin in the methane phase as a result of a second pass.

A second methane phase digester is indicated at 28, and the methane phase effluent is moved to the second methane phase along line 29. As previously stated, improved gasification occurs in the second methane phase from preferential action by micro-organisms, including methanation of carbon dioxide gas which can be returned to the second methane phase along line 30. The gas production from the second methane phase can be delivered to the gas clean-up zone along line 31 and the effluent can be conveyed along line 32 to the effluent zone 11. A sulfide neutralization salt such as ferric chloride can be introduced from sources (not shown) to one or both of the methane phase digesters to neutralize sulfide formation and reduce hydrogen sulfide which occurs in the digester gases.

Following Table I presents a range of optimum conditions which leads to an improved two phase digestion process. The organic waste which is treated can be primary sludge, activated sludge, a mixture of both, manure, solid waste, or industrial waste. The following data represents a delivery of organic waste to an acid phase digester, maintenance and detention of the waste in said digester as set out in the following table, and then delivery of the lower molecular weight acid and intermediate products to a methane phase digester, as well as collection of methane gas in the gasification process in the methane phase digester.

TABLE I

| Nature of Feed | Acid Phase | Methane Phase (Acid Phase effluent) |
|---|---|---|
| 1. Feed Consistency, % total solids | 2–10 | 1–7 |
| 2. Temperature, °C | 20–40 | 20–40+ |
| 3. Culturing Mode | Continuous | Intermittent or Continuous |
| 4. Recycling % of Influent | 0–50* | 0–40* |
| 5. Mixing | Continuous Moderate Agitation | Intermittent or Continuous-Gentle Agitation |
| 6. Residence Time, Day | 0.5–1.5 | 2–7 |
| 7. Loading, lb total organics/CF-day | 1–10 | 0.1–0.5 |
| 8. pH | 5–6 | 6.8–7.4 |
| 9. ORP, mV | 200–300 | 425–550 |

*Concentrated or raw effluent
+Can be operated in thermophilic range, 50–65° C; in this case, the loading can be increased up to 2.0 lb. of total organics/CF-day.

The following Table II presents data collected from feeding activated sludge into separated acid phase and methane phase digesters. The methane content is measured directly from the methane phase.

TABLE II

| A. | Operating Conditions | Acid Phase | Methane Phase |
|---|---|---|---|
| | 1. Feed | Act. Sludge | Acid Effluent |
| | 2. Mode of Operation | Continuous | Daily, Intermittent |
| | 3. Detention time, day | 0.5 | 6.5 |
| | 4. Loading, lb org/CF-day | 1.5–2.7 | 0.2 |
| | 5. Temperature, °C | 35 | 35 |
| | 6. pH | 5.7–5.9 | 7–7.2 |
| B. | Performance | | |
| | 1. Total gas production, CF/lb VS added | 0.02–0.3 | 5–6 |
| | 2. Methane content, % | 19–44 | 70 |
| | 3. Methane production, CF/lb VS added | 0–0.1 | 3.5–4.2 |
| | 4. Denitrification | High | Little |
| | 5. Predominant volatile acid | Acetic | |

The foregoing two phase digestion process, under the conditions recited, results in an increased methane content of the product gas, and the waste processing capacity is increased for a given detention time relative to conventional digestion. The instant process also results in an increased solids destruction and a high rate of denitrification which occurs in the first or acid phase. The effluent leaving the two phase process represents a high level of denitrification, and such effluent contains volatile acid concentrations which are much lower than those occurring in conventional digester effluents. Such desired advantages are realized in the separated acid and methane phases characterized by the short overall detention time and the increased loading, as well as the continuous feed to the acid phase. The features of pre and post hydrolysis lead to desirable embodiments in the practice of the method, as well as the steps of recycling to attain second pass advantages. The recycling feature includes alternatively returning $CO_2$ from the gas clean-up zone 8 via line 33 to the methane phase digester 6. Not only is $CO_2$ returned for subsequent methanation, but the gas activity bubbles the feed in the methane phase to improve agitation and resultant gasification.

The claims of the invention are now presented and the terms of such claims may be further understood by reference to the language of the preceeding specification as well as considering the view of the drawing.

What is claimed is:

1. A method for producing methane gas by a two phase anaerobic digestion of solid organic waste and biomass containing insoluble materials which includes the improved steps of:

continuously delivering said feed to an acid phase digester at a loading rate of about 1 to about 10 lb. total organics per cubic foot-day, fermenting the feed in the acid phase digester under anaerobic conditions for a detention time of about ½ day to about 1½ days, at a ph between about 5-6 and a temperature between about 20°-40° C., conveying the resultant acid effluent to a separate methane phase digester at a loading rate up from about 0.1 to less than about 2 lb. of total organics per cubic foot-day, fermenting the acid effluent in the methane phase digester for a detention time of about 2 to about 7 days, at a ph between about 6.8 – 7.4, and a temperature between about 20°-65° C., removing the methane for collection, and removing the feed effluent from the methane phase digester to process the solid and liquid components of the effluent.

2. A method which includes the improved steps of claim 1 wherein the acid effluent is loaded in the methane phase digester at a rate of about 0.1 lb to about 0.5 lb. of total organics per cubic foot-day.

3. A method which includes the improved steps of claim 1 wherein the acid effluent is loaded in the methane phase digester at a thermophilic range of about 50° to about 65° C at a rate of about 2 lb. per cubic foot-day.

4. A method which includes the improved steps of claim 1 and which further includes hydrolyzing the feed mixture in a prehydrolysis zone, adding a neutralizing agent to the hydrolysed feed mixture, and then delivering the hydrolysed feed mixture to the acid phase digester.

5. A method which includes the steps of claim 4 above wherein effluent from the methane phase digester is recycled to the prehydrolysis zone.

6. A method which includes the improved steps of claim 1 above wherein effluent from the methane phase digester is delivered to a post gasification hydrolysis zone, adding a neutralizing agent to the post hydrolysed effluent, and recycling the post hydrolysed effluent mixture to one of the acid and gas phase digesters.

7. A method which includes the improved steps of claim 1 above wherein the methane digester produces methane and carbon dioxide, and further including the step of conveying such produced gases to a gas clean-up zone to separate substantially methane, and then delivering said substantially separated methane to a collecting pipeline.

8. A method which includes the improved steps of claim 1 above and which further includes the steps of delivering effluent from the methane digester phase to a second methane digester phase, fermenting the effluent in said second methane digester phase, collecting gasification products from said second methane digester phase, and collecting the effluent from said second methane digester phase.

9. A method which includes the improved steps of claim 1 and which further includes collecting methane and carbon dioxide from the methane phase digester, and recycling said carbon dioxide to the methane phase digester for methanation and physical agitation of the mixture therein.

10. A method which includes the improved steps of claim 1 above and which further includes recycling effluent from the methane phase digester to the acid phase digester to denitrify the effluent and to reduce the volatile acids in such effluent.

* * * * *